(12) United States Patent
Moeller

(10) Patent No.: US 7,929,580 B2
(45) Date of Patent: Apr. 19, 2011

(54) INEXPENSIVE TERAHERTZ PULSE WAVE GENERATOR

(75) Inventor: Lothar Benedict Erhard Josef Moeller, Middletown, NJ (US)

(73) Assignee: Alcatel-Lucent USA Inc., Murray Hill, NJ (US)

( * ) Notice: Subject to any disclaimer, the term of this patent is extended or adjusted under 35 U.S.C. 154(b) by 1042 days.

(21) Appl. No.: 11/525,787

(22) Filed: Sep. 22, 2006

(65) Prior Publication Data
US 2008/0075134 A1    Mar. 27, 2008

(51) Int. Cl.
*H01S 3/098* (2006.01)

(52) U.S. Cl. ......... 372/18; 372/24; 372/25; 372/29.016; 372/38.02; 372/43.01; 372/109; 327/181; 327/187; 328/15; 328/17; 328/18; 250/336.1; 250/338.1; 250/338.4; 250/340; 250/341.1; 250/341.8; 324/96; 324/629; 324/630; 324/637; 324/638; 324/765

(58) Field of Classification Search ............. 372/18, 372/24, 25, 29.016, 38.02, 43.01, 109; 327/181, 327/187; 338/15, 17, 18; 250/336.1, 338.1, 250/338.4, 340, 341.1, 341.8; 324/96, 629, 324/630, 637, 638, 765
See application file for complete search history.

(56) References Cited

U.S. PATENT DOCUMENTS

| | | | | |
|---|---|---|---|---|
| 4,127,784 A | * | 11/1978 | Proud et al. | 327/181 |
| 4,156,148 A | * | 5/1979 | Kaufman | 250/551 |
| 4,347,437 A | * | 8/1982 | Mourou | 250/214.1 |
| 4,376,285 A | * | 3/1983 | Leonberger et al. | 338/15 |
| 4,413,178 A | * | 11/1983 | Mourou et al. | 250/214 VT |
| 4,482,863 A | * | 11/1984 | Auston et al. | 324/754.23 |
| 4,665,524 A | * | 5/1987 | Cotter | 372/18 |
| 4,681,449 A | * | 7/1987 | Bloom et al. | 356/364 |
| 4,695,733 A | * | 9/1987 | Pesavento | 250/551 |
| 4,726,031 A | * | 2/1988 | Wakao et al. | 372/96 |
| 4,782,222 A | * | 11/1988 | Ragle et al. | 250/214 R |
| 4,864,119 A | * | 9/1989 | Ragle et al. | 250/214.1 |
| 4,960,989 A | * | 10/1990 | Liebenrood et al. | 250/227.15 |
| 4,978,910 A | * | 12/1990 | Knox et al. | 324/96 |
| 5,056,111 A | * | 10/1991 | Duling et al. | 375/259 |
| 5,142,224 A | * | 8/1992 | Smith et al. | 324/754.23 |
| 5,384,798 A | * | 1/1995 | Zucker et al. | 372/26 |
| 5,486,833 A | * | 1/1996 | Barrett | 342/204 |
| 5,541,947 A | * | 7/1996 | Mourou et al. | 372/25 |
| 5,598,425 A | * | 1/1997 | Jain et al. | 372/18 |
| 5,623,145 A | * | 4/1997 | Nuss | 250/330 |

(Continued)

OTHER PUBLICATIONS

"SubPicosend Photoconducting Dipole Antennas," by Smith et al., IEEE Journal of Quantum Electronics, V. 24., No. 2 (1988), pp. 255-260.*

(Continued)

*Primary Examiner* — Hrayr A Sayadian
(74) *Attorney, Agent, or Firm* — Mendelsohn, Drucker & Associates, P.C.; Yuri Gruzdkov; Steven Mendelsohn

(57) ABSTRACT

Pulses of signals in the terahertz region are generated using an apparatus made up of a mode-locked semiconductor laser diode with a short duty cycle that is optically coupled to a biased Auston switch. The output from the mode-locked semiconductor laser diode may first be supplied to a pulse compressor, and the resulting compressed pulses supplied to the Auston switch. Preferably, the mode-locking of the semiconductor laser diode is controllable, i.e., it is an active mode-locking semiconductor laser, so that the phase of the output optical signal from the laser is locked to the phase of an input control signal.

18 Claims, 1 Drawing Sheet

U.S. PATENT DOCUMENTS

| | | | | |
|---|---|---|---|---|
| 5,778,016 | A * | 7/1998 | Sucha et al. | 372/38.1 |
| 5,844,288 | A * | 12/1998 | Mourou et al. | 257/431 |
| 6,058,128 | A * | 5/2000 | Ventrudo | 372/96 |
| 6,320,367 | B1 * | 11/2001 | Cuzin et al. | 324/96 |
| 6,396,856 | B1 * | 5/2002 | Sucha et al. | 372/25 |
| 6,813,288 | B2 * | 11/2004 | Kim et al. | 372/20 |
| 6,963,442 | B2 * | 11/2005 | Yap et al. | 359/326 |
| 7,095,772 | B1 * | 8/2006 | Delfyett et al. | 372/50.22 |
| 7,212,553 | B2 * | 5/2007 | Starodoumov et al. | 372/4 |
| 7,289,203 | B2 * | 10/2007 | Frankel | 356/301 |
| 7,535,005 | B2 * | 5/2009 | Demers | 250/341.1 |
| 7,605,371 | B2 * | 10/2009 | Yasui et al. | 250/341.8 |
| 2002/0105711 | A1 * | 8/2002 | Kaneko | 359/248 |
| 2005/0111129 | A1 * | 5/2005 | Crawford et al. | 360/68 |
| 2006/0058608 | A1 * | 3/2006 | Hogan | 600/407 |
| 2008/0165355 | A1 * | 7/2008 | Yasui et al. | 356/323 |
| 2008/0314152 | A1 * | 12/2008 | Ouchi | 73/597 |

OTHER PUBLICATIONS

"Subpicosecond Photoconducting Dipole Antennas," by "Smith-1," IEEE Journal of Quantum Electronics, vol. 24, No. 2, (1988), pp. 255-260.*

"Imaging with Terahertz Waves," by "Hu and Nuss," Optics Letters, vol. 20, No. 16 (1995), pp. 1716-1719.*

"Compression of Pulses from a Mode Locked GaAs Laser Diode . . . ," by "Carter," App. Phys. Lett., vol. 61, No. 4 (1992), pp. 379-380.*

WO 2005/001505 A (Canon KK [JP]; Ouchi Toshihiko [JP]) Jan. 6, 2005 p. 37, line 51-p. 38, line 21; figure 15 p. 25, line 6-p. 26.

WO 2005/008211 A (Sarnoff Corp [US]; Trotz Seth [US]; New David A [US]; Braun Alan M [US]) Jan. 27, 2005 paragraph [0025]-paragraph [0029].

Yasui Takeshi et al: "Asynchronous optical sampling terahertz time-domain spectroscopy for ultrahigh spectral resolution and rapid data acquisition" Applied Physics Letters, AIP, American Institute of Physics, Melville, NY, US, vol. 87, No. 6, Aug. 1, 2005, pp. 61101-61101, XP012077361 ISSN: 0003-6951 the whole document.

Whitaker J F et al: "Terahertz-bandwidth pulses for coherent time-domain spectroscopy" Proceedings of The SPIE—The International Society For Optical Engineering USA, vol. 2145, 1994, pp. 168-177, XP002467487 ISSN: 0277-786X Chapter 2. Experimental System.

Janke C et al: "Asynchronous optical sampling for high-speed characterization of integrated resonant THz-biosensors" Optics Letters, OSA, Optical Society of America, Washington, DC, US, vol. 30, No. 11, Jun. 1, 2005, pp. 1405-1407, XP003002055 ISSN: 0146-9592 the whole document.

Vickers A J et al: "A gain switched semiconductor laser pump-probe source" Terahertz Electronics Proceedings, 1998. THZ Ninty Eight. 1998 IEEE Sixth International Conference on Leeds, UK Sep. 3-4, 1998, New York, NY, USA, IEEE, US Sep. 3, 1998, pp. 191-193, XP010314470 ISBN: 0-7803-4903-2 p. 192, right-hand column.

Gong-Ru Lin et al: "Novel electro-optic sampling system with an optoelectronic phase-locked phase shifter as a delay-time controller" Japanese Journal of Applied Physics, Part 1 (Regular Papers, Short Notes & Review Papers) Japan Soc. Appl.Phys Japan, vol. 41, No. 10, Oct. 2002, pp. 6003-6006, XP002467553 ISSN: 0021-4922 Chapter 2. Experimental.

PCT International Search Report dated Feb. 25, 2008 (PCT/US2007/020298).

* cited by examiner

INEXPENSIVE TERAHERTZ PULSE WAVE GENERATOR

TECHNICAL FIELD

This invention relates to the generation of pulses of electromagnetic waves in the terahertz frequency range.

BACKGROUND OF THE INVENTION

Pulses of signals in the so-called "terahertz region", which is also known as the "terahertz gap", e.g., between 300 gigahertz and 10 terahertz, are useful for various applications, e.g., spectrum analyzer and imaging applications. Prior art terahertz pulse wave generators employed a Titanium-sapphire (Ti:Sapphire) laser which generates pulses of light, typically at a carrier wavelength of 780 nm corresponding to approximately 400 terahertz, each pulse having a period typically of between 50 and 300 femtoseconds, i.e., the spectral width of each pulse is approximately 3 terahertz. The pulses are then directed to an optical splitter, which generates two replicas of the pulses. The pulses of one of the replicas is supplied to a biased Auston switch, which responds to the input optical pulses to produce electromagnetic pulses with a spectral width of approximately one to two terahertz. The Auston switch includes an antenna, and possibly a lens, e.g., a silicon lens, to focus the terahertz pulse.

One use of such terahertz pulses is made by having the terahertz pulses being directed at a material under test, e.g., a pharmaceutical product, so that they are reflected back therefrom to a receiving, unbiased Auston switch. The unbiased Auston switch is supplied with a variably delayed version of the second replica of the optical pulses generated by the Titanium-sapphire laser. Typically, a mechanically tunable optical delay line implements the delay. The unbiased Auston switch generates an electrical output in response to a reflected terahertz signal that it receives when it is stimulated by a terahertz optical signal.

The delayed optical pulses of the second replica are used to control the time at which an output is produced by the Auston switch. In other words, the delayed optical pulses of the second replica "gates" the output of the Auston switch, an output being generated therefrom only when an optical pulse of the second replica is received. The delay is changed so that the part of the reflected terahertz pulse to be investigated arrives at the Austin switch as the same time as the gating pulse. Note that each reflected pulse should be the same provided that no changes are made to the first replica or the location of the material under test. Thus, to gain an overall impression of the entirety of a reflected terahertz pulse, the delay in the path of the second replica is changed for each of a sequence of terahertz pulses to scan over the entire width of one of the reflected pulses.

Disadvantageously, the use of a Titanium-sapphire laser is unduly expensive. Also, use of the mechanically tunable delay line makes the measurement slow and relatively expensive. Furthermore, because the delay line is mechanical, the device is less robust, and hence not as suitable to mobile applications, than might be desired.

SUMMARY OF THE INVENTION

I have recognized that the generation of pulses of signals in the terahertz region can be improved, in accordance with the principles of the invention, by an apparatus made up of a mode-locked semiconductor laser diode with a short duty cycle that is optically coupled to a biased Auston switch. In order to improve performance, e.g., to increase the spectral width of the terahertz pulse, i.e., to make them shorter in duration, the output from the mode-locked semiconductor laser diode may first be supplied to a pulse compressor, and the resulting compressed pulses supplied to the Auston switch so as to generate the terahertz pulses. Preferably, the mode locking of the semiconductor laser diode is controllable, i.e., it is an active mode-locking semiconductor laser, so that the phase of the output optical signal from the laser is locked to the phase of an input control signal.

In accordance with an aspect of the invention, investigation of a material may be made using an apparatus which includes a) a first mode-locked semiconductor laser diode, the output of which is coupled to a biased Auston switch so as to generate terahertz pulses which are supplied to the material under test; and b) a second mode-locked semiconductor laser diode, which is optically coupled to an unbiased Auston switch which generates an electrical signal in response to receipt of the terahertz pulses which have contacted, i.e., been reflected from, and/or passed at least in part through, the material under test and laser pulses from the second laser diode. The phase of the mode-lock control of at least one of the lasers may be controllably varied so as to scan over the entire width of one of the contacted pulses, thus achieving the same effect as achieved by the prior art using the mechanically tunable optical delay line.

In accordance with another aspect of the invention, investigation of a material may be made using an apparatus in which the pulses output from a first mode-locked semiconductor laser diode are directed to an optical splitter, which generates two replicas of the pulses. One of the replicas is delayed using a fixed delay, e.g., a fiber or free space delay. The delayed replica and the undelayed replica are each coupled to respective Auston switches, one of which is biased and one of which is not. Scanning is performed by changing the repetition frequency of the pulses generated by the laser diode slightly repetitively in a periodic manner. Over each cycle the result is that the pulses at the output of the delay line are shifted with respect to the undelayed replica.

In order to improve performance, e.g., increase the spectral width of the terahertz pulses, i.e., to make them shorter in duration, the output from each of the mode-locked semiconductor laser diodes may first be supplied to a pulse compressor, and the resulting compressed pulses supplied to the respective, associated Auston switches.

Advantageously, two mode-locked semiconductor laser diodes are cheaper, use less power, are smaller, require less maintenance, and are more portable than a Titanium-sapphire laser. Further advantageously, eliminating the use of the mechanically tunable optical delay line makes the measurement quicker and relatively less expensive. Furthermore, the device is more robust and especially suitable to mobile applications.

DETAILED DESCRIPTION

Figure 1:
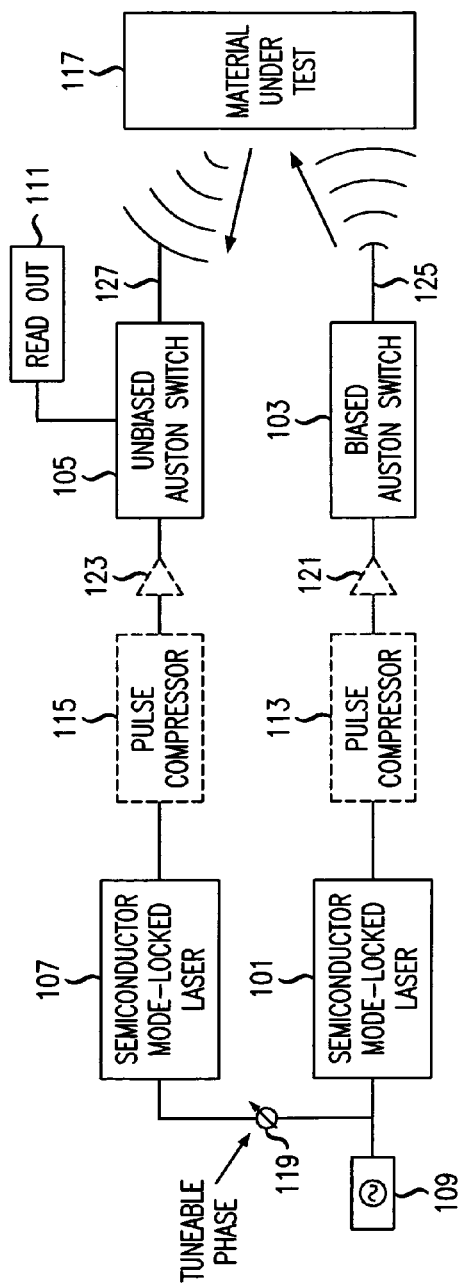
FIG. 1 shows an exemplary arrangement for generating pulses of signals in the terahertz region and for investigating a material, in accordance with the principles of the invention.

The following merely illustrates the principles of the invention. It will thus be appreciated that those skilled in the art will be able to devise various arrangements that, although not explicitly described or shown herein, embody the principles of the invention and are included within its spirit and scope. Furthermore, all examples and conditional language recited herein are principally intended expressly to be only for pedagogical purposes to aid the reader in understanding the principles of the invention and the concepts contributed by the inventor(s) to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

It will be appreciated by those skilled in the art that any block diagrams herein represent conceptual views of illustrative circuitry embodying the principles of the invention. The functions of the various elements shown in the FIGs., including any functional blocks labeled as "processors", may be provided through the use of dedicated hardware as well as hardware capable of executing software in association with appropriate software. When provided by a processor, the functions may be provided by a single dedicated processor, by a single shared processor, or by a plurality of individual processors, some of which may be shared.

In the claims hereof any element expressed as a means for performing a specified function is intended to encompass any way of performing that function. This may include, for example, a) a combination of electrical or mechanical elements which performs that function or b) software in any form, including, therefore, firmware, microcode or the like, combined with appropriate circuitry for executing that software to perform the function, as well as mechanical elements coupled to software controlled circuitry, if any. The invention as defined by such claims resides in the fact that the functionalities provided by the various recited means are combined and brought together in the manner which the claims call for. Applicant thus regards any means which can provide those functionalities as equivalent as those shown herein.

Unless otherwise explicitly specified herein, the drawings are not drawn to scale. Also, unless otherwise explicitly specified herein, all optical elements or systems that are capable of providing specific function within an overall embodiment disclosed herein are equivalent to one another for purposes of the present disclosure.

In the description, identically numbered components within different ones of the FIGs. refer to the same components.

The generation of pulses of signals in the terahertz region is achieved, in accordance with the principles of the invention, by an apparatus made up of a mode-locked semiconductor laser diode with a short duty cycle that is optically coupled to a biased Auston switch. In order to improve performance, e.g., to increase the spectral width of the terahertz pulse, i.e., to make them shorter in duration, the output from the mode-locked semiconductor laser diode may first be supplied to a pulse compressor, and the resulting compressed pulses supplied to the Auston switch so as to generate the terahertz pulses. Preferably, the mode-locking of the semiconductor laser diode is controllable, i.e., it is an active mode-locking semiconductor laser, so that the phase of the output optical signal from the laser is locked to the phase of an input control signal.

FIG. 1 shows an exemplary arrangement for generating pulses of signals in the terahertz region including mode-locked semiconductor laser diode 101 and biased Auston switch 103. Also shown are mode-locking sinusoid generator 109, optional pulse compressor 113, and optional optical amplifier 121.

Mode-locked semiconductor laser diode 101 produces pulses of light, i.e., optical pulses, typically at a carrier wavelength that is employed for telecommunications applications, e.g., 1.5 µm or 1.3 µm, the pulses having a short duty cycle. The carrier frequency of the optical pulses supplied as an output by a laser diode at 1.5 µm is around 200 terahertz. Also, current laser diodes designed for telecommunications applications typically can generate a train of optical pulses in which each pulse has a width of around 1 picosecond, and the pulse repetition rate is approximately 40 gigahertz, although custom laser diodes could be designed with shorter pulse widths. In the frequency domain, the output from mode-locked semiconductor laser diode 101 is a lobe centered at the optical carrier frequency of 200 terahertz and having a width of around 1 terahertz. Preferably, the mode-locking of mode-locked semiconductor laser diode 101 is controllable, i.e., it is an active mode-locking semiconductor laser, so that the phase of the output optical signal from the laser is locked to the phase of an input control signal.

Mode-locking sinusoid generator 109 generates a sinusoidal mode locking signal which is supplied as an input control signal to mode-locked semiconductor laser diode 101. The frequency of sinusoidal mode locking signal is typically around 40 gigahertz. The sinusoidal mode locking signal controls the phase of the pulses produced by mode-locked semiconductor laser diode 101. Mode-locked semiconductor laser diode 101 is optically coupled, e.g., via fiber, free space, or a combination thereof, to biased Auston switch 103.

Biased Auston switch 103 responds to the optical pulses incident upon it to produce electromagnetic pulses in the terahertz region. More specifically, biased Auston switch 103 responds to the optical pulses by producing a pulsed electromagnetic signal with the same repetition rate as the frequency of sinusoidal mode locking signal and an approximate width of 1 picosecond, and hence with frequency components in the terahertz range. Biased Auston switch 103 may be biased with a continuous voltage. The output of biased Auston switch 103 may be coupled to an antenna, e.g., antenna 125, so that the resulting electrical signal causes an electromagnetic wave having a frequency in the terahertz range to propagate from antenna 125, e.g., radiated into space. Alternatively, the resulting electrical signal may be captured by a focusing device, e.g., a lens or an antenna, and supplied to a waveguide, e.g., in order to contain the terahertz waves that are produced on a chip.

Optional pulse compressor 113 makes the pulses shorter in duration, thus, correspondingly, increasing their spectral width, which may increase performance. Optional pulse compressor 113 receives the optical pulses from mode-locked semiconductor laser diode 101 and supplies the compressed pulses to biased Auston switch 103. As is well known in the art, pulse compressor 113 may be made up of a nonlinear optical waveguide coupled to a chromatic dispersion compensator.

Optional optical amplifier 121, e.g., an erbium doped fiber amplifier or a semiconductor optical amplifier, amplifies the optical signal it receives and supplies the amplified version to biased Auston switch 103.

In accordance with an aspect of the invention, investigation of a material, e.g., material under test 117 shown in FIG. 1, may be made using the electromagnetic terahertz pulses generated by biased Auston switch 103 by directing them to "contact" material under test 117 and analyzing at least a portion of the electromagnetic terahertz pulses after the contact. Note that a pulse has "contacted" the material being investigated when it has been reflected from, and/or passed at least in part through, the material. Components shown in FIG. 1 that are useful for investigation of a material are 1) second mode-locked semiconductor laser diode 107, 2) unbiased Auston switch 125, 3) optional phase tuner 119, 4) optional pulse compressor 115, and 5) optional optical amplifier 123.

Preferably identical to mode-locked semiconductor laser diode 101, mode-locked semiconductor laser diode 107 produces pulses of light, typically at a carrier wavelength that is employed for telecommunications applications, e.g., 1.5 µm or 1.3 µm, the pulses having a short duty cycle. The carrier frequency of the optical pulses supplied as an output by a laser diode at 1.5 µm is around 200 terahertz. As noted hereinabove, current laser diodes designed for telecommunications applications typically can generate a train of optical pulses in which each pulse has a width of around 1 picosecond, and the pulse repetition rate is approximately 40 gigahertz. In the frequency domain, the output from mode-locked semiconductor laser diode 107 is a lobe centered at the optical carrier frequency of 200 terahertz and having a width of around 1 terahertz. Preferably, the mode locking of mode-locked semiconductor laser diode 107 is controllable, i.e., it is an active mode-locking semiconductor laser, so that the phase of the output optical signal from the laser is locked to the phase of an input control signal.

Mode-locked semiconductor laser diode 107 is supplied with the sinusoidal mode locking signal produced by mode-locking sinusoid generator 109 after it is modified by optional phase tuner 119. Thus, it is the modified sinusoidal mode locking signal that is supplied as an input control signal to mode-locked semiconductor laser diode 107 to control the phase of the pulses it produces. Mode-locked semiconductor laser diode 107 is optically coupled, e.g., via fiber, free space, or a combination thereof, to unbiased Auston switch 105.

Unbiased Auston switch 105 produces an electrical output in response to 1) the optical pulses incident upon it and 2) an electromagnetic signal that is a portion of the energy of the electromagnetic pulses that were generated by biased Auston switch 103 and made contact with material 117. The electromagnetic signal that made contact with material 117 is received via optional antenna 127, which focuses the energy and directs it to unbiased Auston switch 105.

More specifically, each optical pulse incident on unbiased Auston switch 105 causes carriers to develop therein. Typically, up until saturation, the stronger the incident optical pulse, the more carriers that are generated. These carriers are swept to the output, i.e., readout 111, by an electromagnetic field created in unbiased Auston switch 105 in response to the signal received thereby from material under test 117. Thus, the time at which an output is produced by unbiased Auston switch 105 is controlled by mode-locked semiconductor laser diode 107, because even when an electromagnetic signal is being received, so as to cause creation of an electromagnetic field within unbiased Auston switch 105, unless there are carriers that were generated therein, no output will be produced. Similarly, even though carriers may have been generated in response to an optical pulse, if no electromagnetic signal is received by unbiased Auston switch 105 then no output will be generated. Note that the density of the carriers produced that will reach the output is a function, e.g., proportional to the strength, of the electromagnetic signal that is received.

The electromagnetic signal that is received at unbiased Auston switch 105 is typically wider than the electromagnetic signal that contacted the material under test. In order to develop a representation of the entire electromagnetic signal that is received at unbiased Auston switch 105 it is necessary to obtain an output value from unbiased Auston switch 105 of the received signal at various points in time. Conceptually, this may be thought of as sampling the electromagnetic signal. However, only one sample may be taken for each pulse of laser diode 107, and so an instantaneous snapshop of the whole received electromagnetic signal cannot be obtained. This problem is overcome by recognizing that generally, for each of a set of substantially identical terahertz pulses launched from biased Auston switch 103, unbiased Auston switch 105 will receive a set of electromagnetic signals that are substantially identical to each other. Thus, it is possible to sample each of the many different identical ones of such received electromagnetic signals at different times in order to construct a representation of a single received pulse.

The times at which each measurement is taken is set by the time at which laser diode 107 generates its optical pulse, thereby causing the generation of carriers in unbiased Auston switch 105. Phase tuner 119 in turn controls the time at which laser diode 107 generates each of its optical pulses. Thus, by changing the phase of the sinusoidal mode locking signal supplied to laser diode 107, phase tuner 119 can cause samples to be taken at times extending over the entirety of the width of a reflected pulse, thus achieving the same effect as achieved by the prior art using the mechanically tunable optical delay line. Since, in practice, the phase may be varied essentially continuously, it is possible to obtain an essentially continuous waveform for the electromagnetic signal. As will be readily recognized by one of ordinary skill in the art, read out 111 may perform sampling for the purposes of digitalization and subsequent analysis.

Although it has been shown and described to change the phase of the mode locking signal supplied to mode-locking semiconductor laser diode 107, those of ordinary skill in the art will readily recognize that the phase of that mode locking signal may be kept constant and instead the phase of the mode locking signal supplied to mode-locking semiconductor laser diode 101 may be varied. Thus, it is only required that the phase of the mode-lock control of at least one of the lasers may be controllably varied so as to scan over the entire width of one of the reflected pulses.

Note that in order to improve the overall measurement and reduce noise, it may be desirable to take readings for the same time during multiple received electromagnetic signals and average those readings together before moving on to the next time.

Optional pulse compressor 115 makes the pulses shorter in duration, thus, correspondingly, increasing their spectral width, which may increase performance. Optional pulse compressor 115 receives the optical pulses from mode-locked semiconductor laser diode 107 and supplies the compressed pulses to unbiased Auston switch 105. One of ordinary skill in the art will readily recognize that, preferably, a given embodiment should employ both optional pulse compressors 113 and 115, which should have the same characteristics. As is well known in the art, pulse compressor 115 may be made up of a nonlinear optical waveguide coupled to a chromatic dispersion compensator.

Optional optical amplifier 123, e.g., an erbium doped fiber amplifier or semiconductor optical amplifier, amplifies the optical signal it receives and supplies the amplified version to unbiased Auston switch 105. One of ordinary skill in the art will readily recognize that, preferably, a given embodiment should employ both optional optical amplifiers 121 and 123, which should have the same characteristics.

Advantageously, two mode-locked semiconductor laser diodes are cheaper, use less power, are smaller, require less maintenance, and are more portable than a Titanium-sapphire such as was required by prior art systems. Further advantageously, eliminating the use of the mechanically tunable optical delay line makes the measurement quicker and relatively less expensive. Even further advantageously, the device is more robust and is especially suited for mobile applications.

Figure 2:
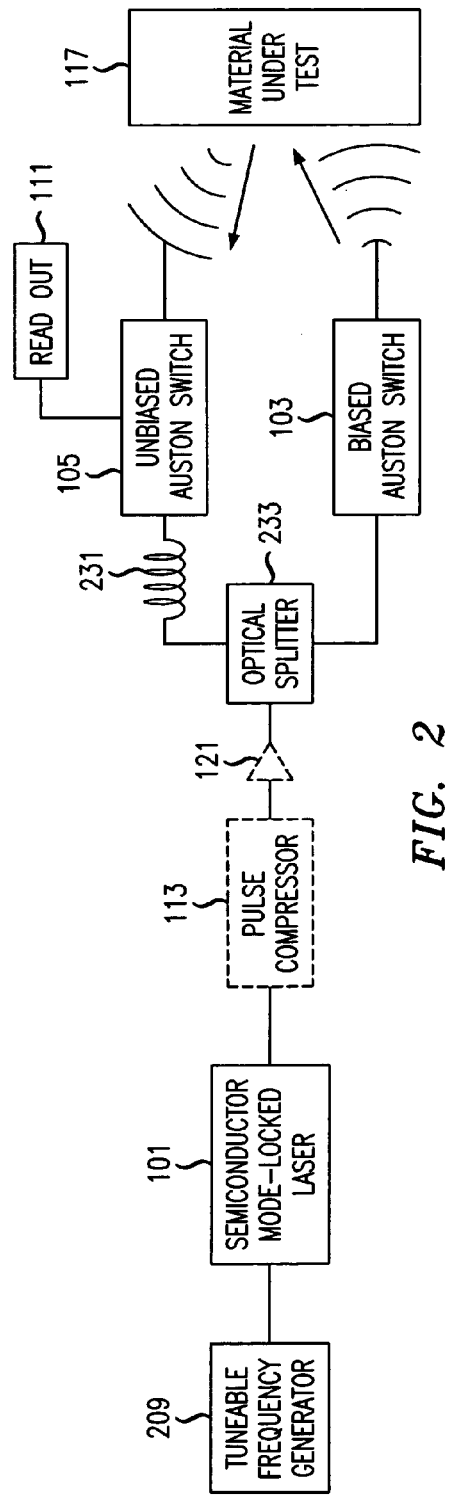
FIG. 2 shows another exemplary arrangement for generating pulses of signals in the terahertz region and for investigating a material in accordance with the principles of the invention.

FIG. 2 shows another exemplary arrangement for investigating a material in accordance with the principles of the invention. Shown in FIG. 2 are 1) mode-locked semiconductor laser diode 101, 2) biased Auston switch 103, 3) unbiased Auston switch 105, 4) tunable frequency generator 209; 5) optical delay 231, 6) optional pulse compressor 113, 7) optical amplifier 121, 8) optical splitter 233, 9) material under test 117, and readout 111.

Mode-locked semiconductor laser diode 101, produces pulses of light, which are optically coupled to biased Auston switch 103. To this end, the light pulses pass through splitter 233, which splits the light pulses into two streams, thus developing two replicas of the originally received pulse train, a first of which propagates to biased Auston switch 103. Prior to reaching optical splitter 233, the light pulses may pass through optional pulse compressor 113 and/or optional amplifier 121, whichever may be employed. The light pulses of the second replica produced by optical splitter 233 pass through optical delay 231 and then on to unbiased Auston switch 105. Preferably, optical delay 231 has a delay of about 10 ns. Optical delay 231 may be implemented as a fiber or a free-space delay.

Mode-locked semiconductor laser diode 101 is supplied with a sinusoidal mode locking signal by tunable frequency generator 209. The frequency of sinusoidal mode locking signal is typically in the 40 gigahertz range, but it is controllably variable. The sinusoidal mode locking signal controls the frequency of the pulses produced by mode-locked semiconductor laser diode 101.

Operationally, the path from laser diode 101 to biased Auston switch 103 functions the same as the corresponding path in FIG. 1, with the exception that only half of the generated light reaches biased Auston switch 103 due to the presence of optical splitter 233. Similarly, light pulses reach unbiased Auston switch 105 after optical splitter 233 via delay 231.

Scanning the electromagnetic signal that is received at biased Auston switch 103 so as to develop an output in a manner similar to that described hereinabove in connection with FIG. 1 is performed by slightly changing the frequency of the mode-locking signal generated by tunable frequency generator 209, which in turn slightly changes the repetition frequency of the pulses generated by laser diode 101. Note that, preferably, the product of the time delay of delay optical delay 231 and the maximum frequency shift should be approximately 1, so that when the delay of optical delay 231 is 10 ns, the frequency change is 100 MHz. The slight change in frequency is performed repetitively in a periodic manner. In other words, the frequency, initially at a nominal value, is changed, either increased or decreased, by, for example 100 MHz. It may then be jumped back to its original value, or it may sweep in reverse back to its original value. Over each cycle of the change in frequency the pulses at the output of the delay line appear to shift continuously in time with respect to the pulses of the undelayed replica.

Note that although optical delay 231 is shown in the path of the replica supplied to unbiased Auston switch 105, as will be readily recognized by one of ordinary skill in the art, alternatively optical delay 231 could be coupled be in the path of the replica supplied to biased Auston switch 103.

What is claimed is:

1. Apparatus for generating pulses of electromagnetic signals in a terahertz region, comprising:
   a mode-locking generator for supplying a first electrical signal and a second electrical signal, said mode-locking generator operatively arranged to shift a phase of the first electrical signal to generate the second electrical signal;
   a first mode-locked semiconductor laser diode for supplying first pulses of light, with the mode-locking of said first semiconductor laser diode controllable so that a phase of the first pulses of light is controlled by the first electrical signal;
   a first Auston switch optically coupled to said first laser diode, said first Auston switch being biased so that, when said first pulses of light from said first laser diode are incident on said first Auston switch, corresponding electromagnetic pulses are generated in the terahertz region;
   a second mode-locked semiconductor laser diode for supplying second pulses of light, with the mode-locking of said second semiconductor laser diode controllable so that a phase of the second pulses of light is controlled by the second electrical signal; and
   a second Auston switch optically coupled to said second laser diode to receive said second pulses of light, said second Auston switch being unbiased and being arranged to receive at least a portion of the energy of said terahertz region pulses.

2. The invention as defined in claim 1 wherein said first mode-locking semiconductor laser diode has a carrier wavelength of one of the group of 1.3 and 1.5 microns.

3. The invention as defined in claim 1, wherein said second mode-locking semiconductor laser diode has a carrier wavelength of about 1.3 or about 1.5 microns.

4. The invention as defined in claim 1, wherein said at least a portion of the energy of said terahertz region pulses received by said unbiased Auston switch has contacted a material being investigated.

5. The invention as defined in claim 1, further comprising a controller for controlling a phase offset between the phase of the first pulses of light and the phase of the second pulses of light, wherein the controller includes the mode-locking generator.

6. The invention as defined in claim 5 wherein said controller adjusts a sinusoidal mode-locking signal supplied to at least one of said first and second laser diodes.

7. A method for generating pulses of signals in a terahertz region, the method comprising the steps of:
   supplying pulses of light from a first mode-locked semiconductor laser diode whose optical output is mode-locked to an electrical control signal;
   generating, in a biased Auston switch electromagnetic pulses in the terahertz region, each of said electromagnetic pulses in the terahertz region switch being generated in response to a corresponding one of said pulses of light from said first laser diode;
   receiving, at an unbiased Auston switch, at least a portion of said electromagnetic pulses in the terahertz region;
   phase-shifting the electrical control signal in a phase tuner to generate a modified electrical signal; and
   receiving at said unbiased Auston switch pulses of light supplied by a second mode-locked semiconductor laser diode whose optical output is mode-locked to the modified electrical signal.

8. The invention as defined in claim 7, further comprising the step of amplifying in power the pulses of light supplied by at least one of the first and second laser diode.

9. The invention as defined in claim 7, further comprising the step of compressing in duration the pulses of light supplied by at least one of the first and second laser diodes.

10. The invention as defined in claim 7, wherein said supplied pulses of light have a carrier wavelength of about 1.3 or 1.5 microns.

11. The invention as defined in claim 7, wherein said at least a portion of the energy of said terahertz region pulses received by said unbiased Auston switch has contacted a material being investigated.

12. The invention as defined in claim 7, further comprising the step of changing a phase offset produced by the phase tuner.

13. Apparatus for generating pulses of signals in a terahertz region, comprising:
   a first mode-locked semiconductor laser diode whose optical output is mode-locked to an electrical control signal, said first laser diode supplying first pulses of light;
   means for generating electromagnetic pulses in the terahertz region, each of said electromagnetic pulses in the terahertz region switch being generated in response to a corresponding one of said first pulses of light;
   a phase tuner adapted to phase-shift the electrical control signal to generate a modified electrical signal; and
   a second mode-locked semiconductor laser diode whose optical output is mode-locked to the modified electrical signal, said second laser diode supplying second pulses of light; and
   means for generating an electronic output signal in response to receipt of at least a portion of said electromagnetic pulses in the terahertz region and said second pulses of light.

14. The invention as defined in claim 13, wherein said at least a portion of said electromagnetic pulses in the terahertz region is received after said electromagnetic pulses in the terahertz region contacted a material under test.

15. The invention as defined in claim 13, wherein the phase tuner is adapted to change the phase shift between the electrical control signal and the modified electrical signal to change temporal offset between said first and second pulses of light.

16. The invention as defined in claim 13, further comprising one or more pulse compressors adapted to compress in duration the first or second pulses of light, or both the first and second pulses of light.

17. The invention as defined in claim 13, wherein:
   the means for generating the electromagnetic pulses in the terahertz region comprises a biased Auston switch; and
   the means for generating the electronic output signal comprises an unbiased Auston switch.

18. The invention as defined in claim 13, wherein:
   the first mode-locked semiconductor laser diode is adapted to supply the first pulses of light having a carrier wavelength of about 1.3 or 1.5 microns; and
   the second mode-locked semiconductor laser diode is adapted to supply the second pulses of light having a carrier wavelength of about 1.3 or 1.5 microns.

* * * * *